United States Patent
Bix et al.

(10) Patent No.: US 7,497,591 B1
(45) Date of Patent: Mar. 3, 2009

(54) EYESTRAIN REDUCING DEVICE

(76) Inventors: James L. Bix, 211 W. Stanley St., Throp, WI (US) 54771; Ginny D. Bix, 211 W. Stanley St., Thorp, WI (US) 54771

( * ) Notice: Subject to any disclaimer, the term of this patent is extended or adjusted under 35 U.S.C. 154(b) by 0 days.

(21) Appl. No.: 11/749,960

(22) Filed: May 17, 2007

(51) Int. Cl.
*F21V 33/00* (2006.01)

(52) U.S. Cl. .............. 362/231; 362/184; 362/200; 362/228

(58) Field of Classification Search ............ 362/228, 362/230, 231, 200, 184
See application file for complete search history.

(56) References Cited

U.S. PATENT DOCUMENTS

| | | | | |
|---|---|---|---|---|
| 6,019,482 A | * | 2/2000 | Everett | 362/184 |
| 6,280,045 B1 | * | 8/2001 | Anteby et al. | 362/103 |
| 6,733,150 B1 | * | 5/2004 | Hanley | 362/106 |
| 6,767,110 B2 | * | 7/2004 | Cooper et al. | 362/184 |
| 2004/0222947 A1 | * | 11/2004 | Newton et al. | 345/39 |

* cited by examiner

*Primary Examiner*—Laura Tso

(57) ABSTRACT

An eyestrain reducing device is disclosed. An illustrative embodiment of the eyestrain reducing device includes a lighting unit having a lighting unit housing; a plurality of light openings provided in the lighting unit housing; and a plurality of lights provided in the lighting unit housing adjacent to the plurality of light openings, respectively. At least one of the plurality of lights is an infrared light. A power source is connected to the plurality of lights. A switch is provided on the light unit housing and electrically connected between the power source and the plurality of lights.

11 Claims, 4 Drawing Sheets

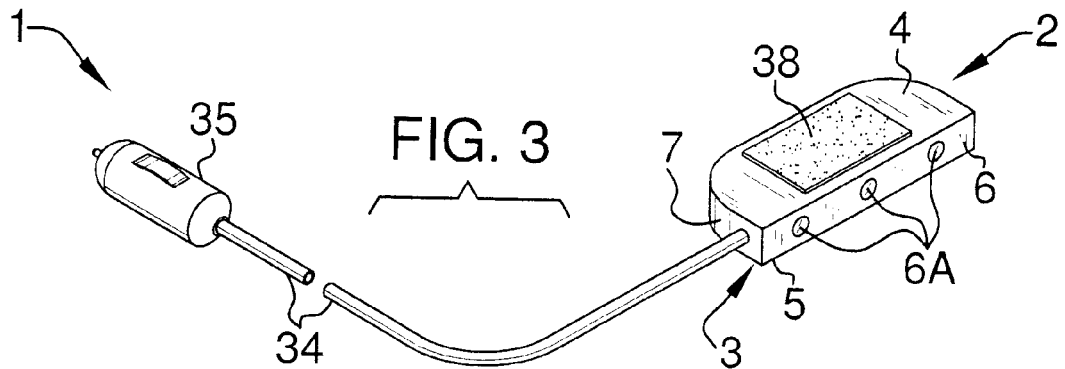
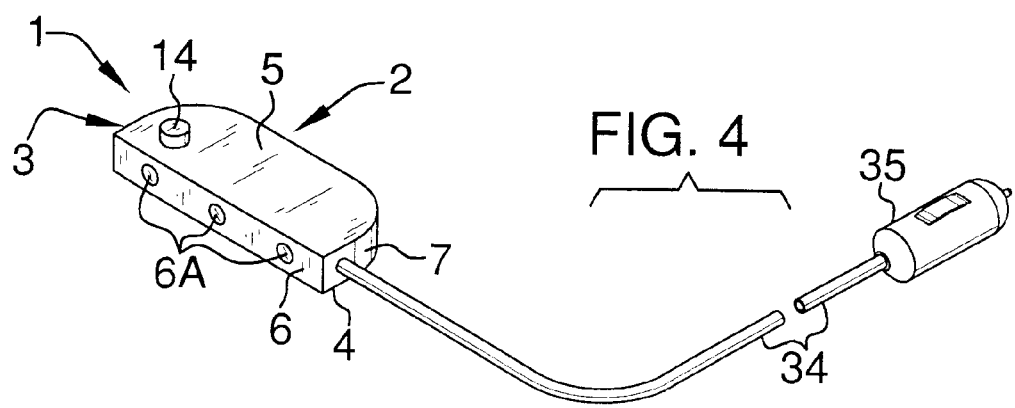
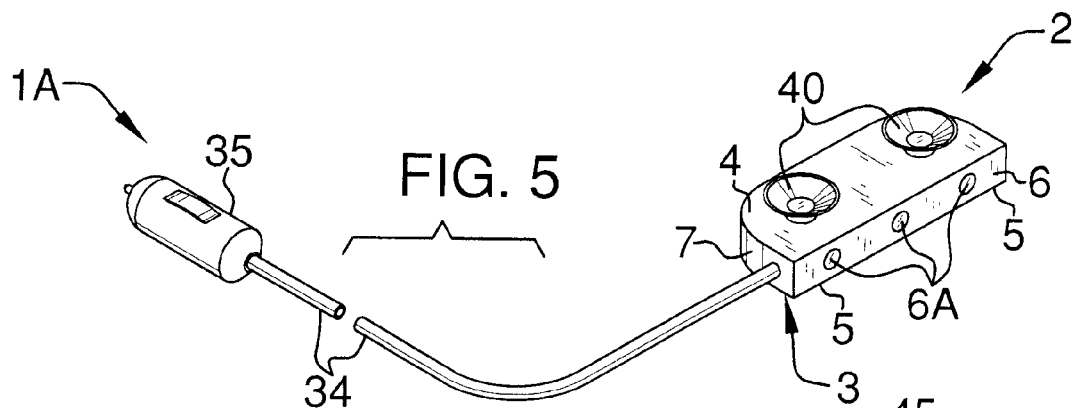
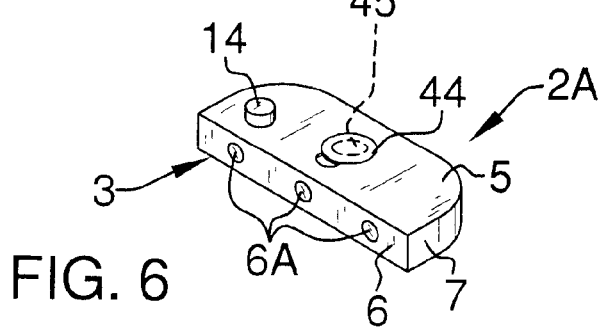

US 7,497,591 B1

EYESTRAIN REDUCING DEVICE

FIELD

The present invention relates to lighting devices for reducing driver eye fatigue during driving. More particularly, the present invention relates to an eyestrain reducing device which can be detachably attached to a vehicle to reduce eyestrain by providing a focal point for a vehicle driver's eyes during driving.

BACKGROUND

Eyestrain is common among drivers during nighttime driving due to lack of a close focal point for the driver's eyes. The resulting eye fatigue may potentially result in an accident, particularly during long stretches of driving. Therefore, an eyestrain reducing device is needed which can be detachably attached to a vehicle to reduce eyestrain by providing a focal point for a vehicle driver's eyes during driving.

SUMMARY

The present invention is generally directed to an eyestrain reducing device. An illustrative embodiment of the eyestrain reducing device includes a lighting unit having a lighting unit housing; a plurality of light openings provided in the lighting unit housing; and a plurality of lights provided in the lighting unit housing adjacent to the plurality of light openings, respectively. At least one of the plurality of lights is an infrared light. A power source is connected to the plurality of lights. A switch is provided on the light unit housing and electrically connected between the power source and the plurality of lights.

BRIEF DESCRIPTION OF THE DRAWINGS

The invention will now be described, by way of example, with reference to the accompanying drawings, in which:

FIG. 3 is a top perspective view, partially in section, of an illustrative embodiment of the eyestrain reducing device, with a hook-and-loop fastener provided on the lighting unit element of the device;

FIG. 4 is a bottom perspective view, partially in section, of an illustrative embodiment of the eyestrain reducing device;

FIG. 5 is a top view of an alternative illustrative embodiment of the eyestrain reducing device, with a pair of suction cups provided on the lighting unit element of the device;

FIG. 6 is a bottom perspective view of a lighting unit element of an alternative illustrative embodiment of the device;

DETAILED DESCRIPTION

Figure 7:
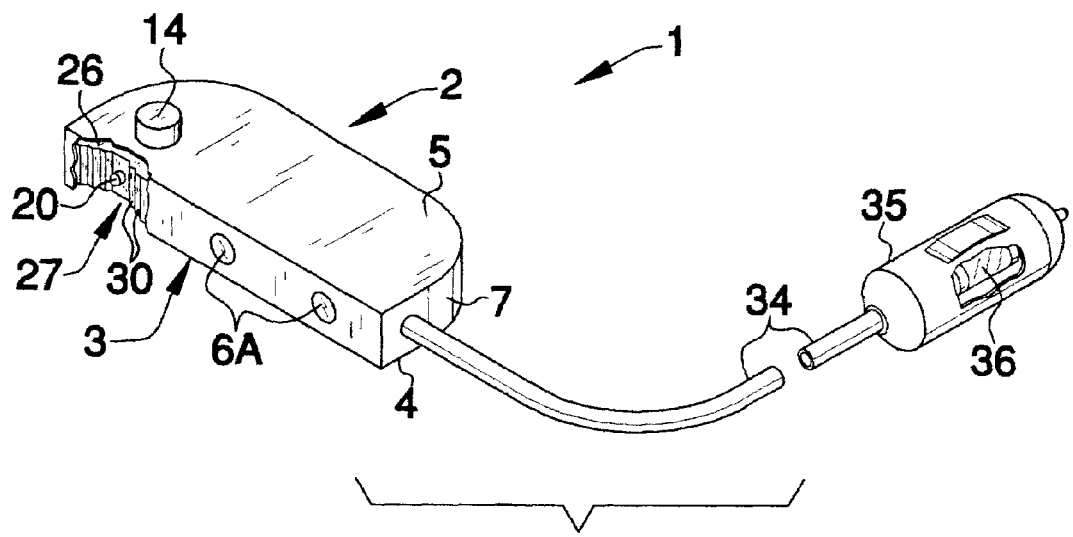
FIG. 7 is a perspective view, partially in section, of an illustrative embodiment of the eyestrain reducing device, more particularly illustrating a stepped reflector surface provided in the lighting unit element and a fuse provided in a plug element of the device.

Referring initially to FIGS. 3-8 of the drawings, an illustrative embodiment of the eyestrain reducing device, hereinafter device, is generally indicated by reference numeral 1. The device 1 includes a lighting unit 2. As shown in FIGS. 3 and 7, the lighting unit 2 includes a lighting unit housing 3 which may have a generally elongated shape. The lighting unit housing 3 includes an attachment panel 4, a switch panel 5 which is spaced-apart and generally parallel with respect to the attachment panel 4. A generally elongated, planar light panel 6 extends between the attachment panel 4 and the switch panel 5. A rear panel 7, which may be curved, also extends between the attachment panel 4 and the switch panel 5. An attachment device, such as a hook-and-loop fastener 38, for example, is provided on the attachment panel 4 of the lighting unit housing 3. As shown in FIG. 5, in an alternative embodiment of the device 1a, the attachment device includes at least one suction cup 40 provided on the attachment panel 4.

Figure 8:
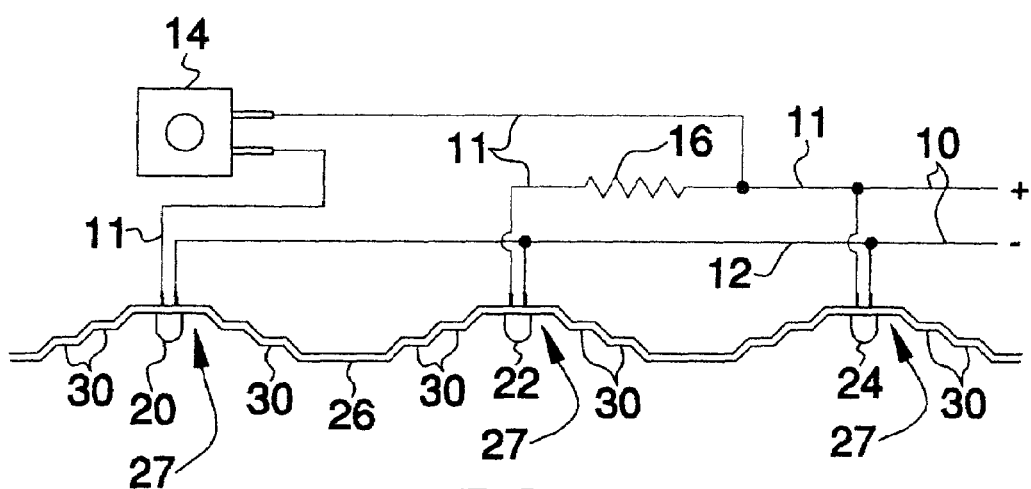
FIG. 8 is a schematic wiring diagram of an illustrative embodiment of the eyestrain reducing device.

Multiple light openings 6a are provided in the light panel 6 in spaced-apart relationship with respect to each other for purposes which will be hereinafter described. As shown in FIGS. 7 and 8, in some embodiments, a reflector panel 26 is provided in the lighting unit housing 3, adjacent to the light panel 6. Multiple light cavities 27, each of which has a stepped reflector surface 30, are provided in the reflector panel 26 and interface with the respective light openings 6a. Lights 20, 22 and 24 extend through respective light openings (not shown) provided in the reflector panel 26 and into the respective light cavities 27 at the respective light openings 6a. In some embodiments, each of the lights 20, 24 is an LED whereas the light 22 is an infrared light. A power source 10 is connected to each light 20, 22 and 24 through a positive lead 11 and a negative lead 12. A resistor 16, which may be a 75-ohm resistor, for example, may be provided in the positive lead 11 between the power source 10 and the infrared light 22. A switch 14 is provided in the positive lead 11, as shown, or alternatively, in the negative lead 12 to reversibly establish electrical power between the power source 10 and each light 20, 22 and 24. The switch 14 extends through a switch opening (not shown) provided in the switch panel 5 of the lighting unit housing 3. While three lights 20, 22 and 24 are shown in the device 1, with two of the lights 20, 24 emitting visible light and one of the lights 22 emitting infrared light, it is to be understood that a greater or fewer number of lights, each of which may emit visible light or infrared light, may be provided in the lighting unit 2.

Figure 1:
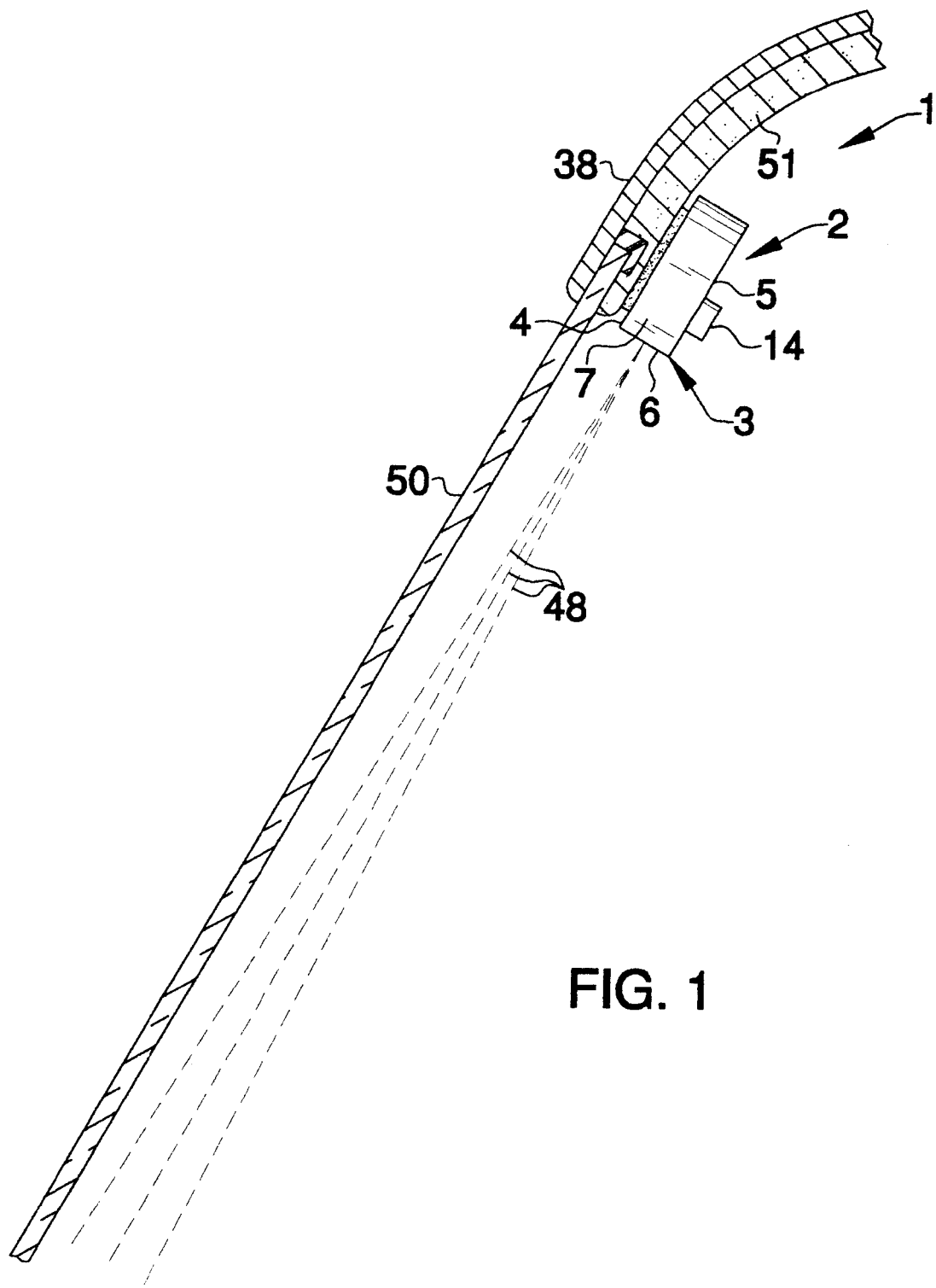
FIG. 1 is a side view of an illustrative embodiment of the eyestrain reducing device, mounted on an interior surface of a vehicle windshield frame (shown in section) and emitting light adjacent to a windshield (shown in section), more particularly illustrating attachment of a lighting unit element of the device to the windshield frame using hook-and-loop fasteners.

In some embodiments, the power source 10 is a 12-volt DC vehicle electrical outlet (not shown). Accordingly, a power cord 34 is electrically connected to the positive lead 11 and the negative lead 12 and extends from the lighting unit housing 3 through a cord opening (not shown) provided in the rear panel 7. A plug 35 is provided on the end of the power cord 34. As shown in FIG. 7, a fuse 36 is typically provided in the internal electrical pathway of the plug 35. Accordingly, upon insertion of the plug 35 into the vehicle electrical outlet (not shown) and manipulation of the switch 14 to the "on" position, electrical power flows through the plug 35, power cord 34 and switch 14 to the respective lights 20, 22 and 24, which emit light rays 48 (FIG. 1). In typical application, each of the lights 20, 24 emits light rays 48 within the visible light range of the light spectrum whereas the typically infrared light 22 emits light rays 48 in the infrared range of the light spectrum. The stepped reflector surface 30 in each light cavity 27 reflects the light rays 48 through the corresponding light opening 6a provided in the light panel 6. Upon manipulation of the switch 14 to the "off" position, flow of electrical power to the lights 20, 22 and 24 is terminated, thereby extinguishing the lights 20, 22 and 24. As shown in FIG. 6, in other embodiments of the device, the power source 10 includes a battery compartment 44 provided in the lighting unit 2a and a battery 45 (shown in phantom) provided in the battery compartment 44. The battery 45 may be replaceable or rechargeable.

Figure 2:
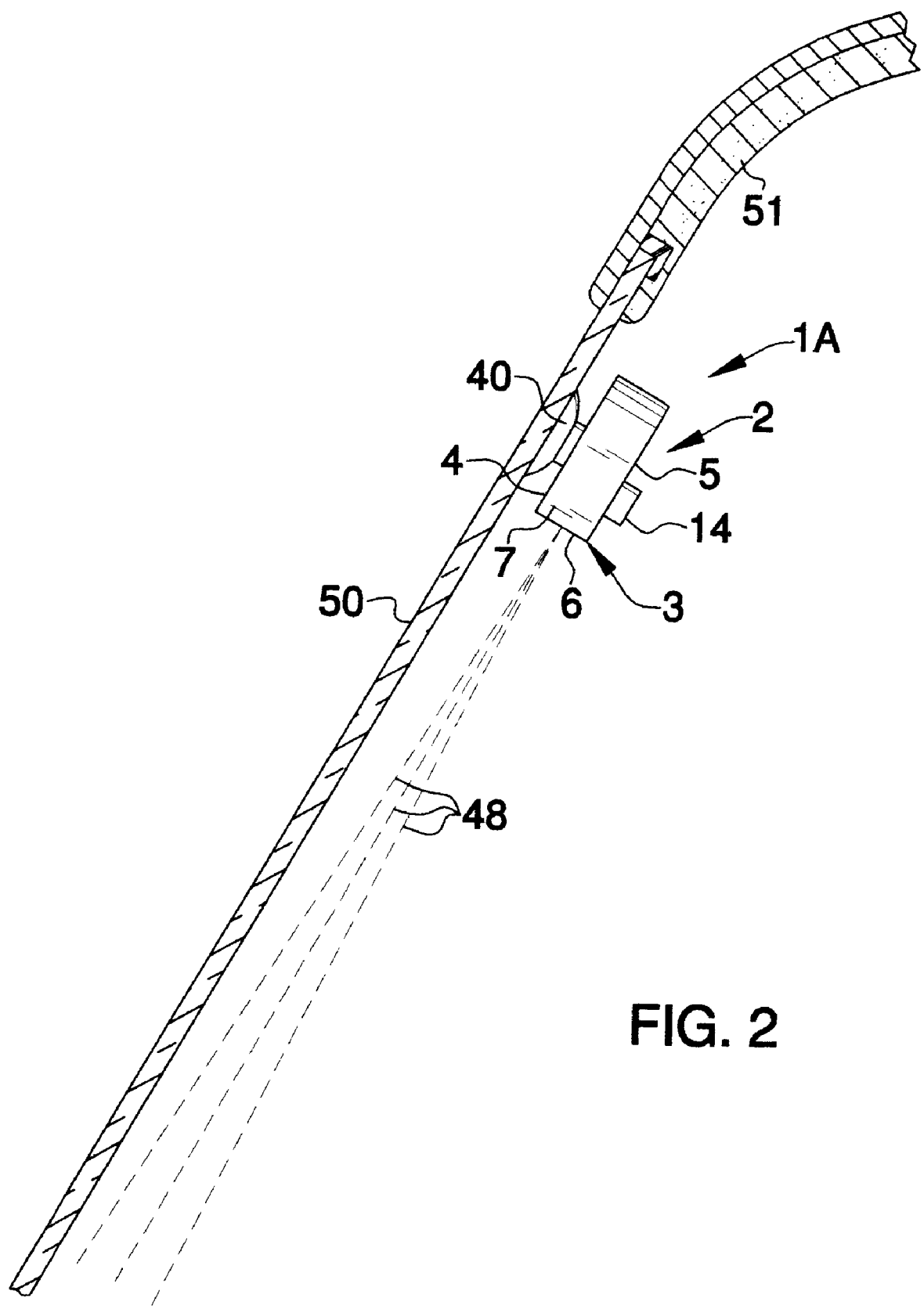
FIG. 2 is a side view of an illustrative embodiment of the eyestrain reducing device, mounted on an interior surface of a vehicle windshield frame (shown in section) and emitting light adjacent to a windshield (shown in section), more particularly illustrating attachment of a lighting unit element of the device to the windshield frame using suction cups.

Referring next to FIGS. 1 and 2 of the drawings, in typical application of the device 1, the lighting unit housing 3 of the lighting unit 2 is attached to an interior surface of a windshield frame 51 of a vehicle, typically above a vehicle windshield 50 which is secured by the windshield frame 51. The lighting unit housing 3 of the device 1 is attached to the windshield frame 51 typically using the hook-and-loop fastener 38, as shown in FIG. 1, whereas the lighting unit housing 3 of the device 1a is attached to the windshield frame 51 typically using the at least one suction cup 40, as shown in FIG. 2. In the embodiment of the device 1 having the 12-volt DC vehicle electrical outlet (not shown) as the power source 10, the plug 35 provided on the power cord 34 is inserted in the DC vehicle electrical outlet. The switch 14 is actuated from the "off" position to the "on" position to illuminate the lights 20, 22 and 24, respectively, each of which emits a light ray 48 through the corresponding light opening 6a provided in the light panel 6 of the lighting unit housing 3, adjacent to the vehicle windshield 50. Accordingly, during nighttime driving, the light rays 48 provide a close focal point for the driver (not shown) of the vehicle, preventing or minimizing eye fatigue. The lights 20, 22 and 24 are extinguished, as desired, by manipulating the switch 14 from the "on" position to the "off" position. The lighting unit housing 3 of the lighting unit 2 can be selectively detached from the interior surface of the windshield frame 51, as desired.

While the preferred embodiments of the invention have been described above, it will be recognized and understood that various modifications can be made in the invention and the appended claims are intended to cover all such modifications which may fall within the spirit and scope of the invention.

What is claimed is:

1. An eyestrain reducing device, comprising:
    a lighting unit having a lighting unit housing;
    a plurality of light openings provided in said light unit housing; said lighting unit housing comprises a first panel; a second panel disposed in generally parallel spaced-apart relationship with respect to said first panel; a rear panel extending between said first panel and said second panel; a generally planar light panel extending between said first panel and said second panel in spaced-apart relationship with respect to said rear panel; and wherein said plurality of light openings is provided in said light panel adjacent to said plurality of lights, respectively;
    a plurality of lights provided in said light unit housing adjacent to said plurality of light openings, respectively;
    wherein at least one of said plurality of lights is an infrared light;
    a power source connected to said plurality of lights; and
    a switch provided on said light unit housing and electrically connected between said power source and said plurality of lights.

2. The eyestrain reducing device of claim 1 wherein said switch is provided on said first panel.

3. The eyestrain reducing device of claim 1 further comprising an attachment device provided on said second panel.

4. The eyestrain reducing device of claim 3 wherein said attachment device comprises a hook-and-loop fastener.

5. The eyestrain reducing device of claim 3 wherein said attachment device comprises at least one suction cup.

6. The eyestrain reducing device of claim 1 further comprising a power cord connected to said plurality of lights and said switch and extending from said lighting unit housing and a plug provided on said power cord.

7. The eyestrain reducing device of claim 1 further comprising a battery compartment provided in said lighting unit housing and wherein said power source comprises a battery provided in said battery compartment.

8. The eyestrain reducing device of claim 1 further comprising a reflector panel having a plurality of light cavities provided in said lighting unit housing adjacent to said plurality of light openings, respectively, and a stepped reflector surface provided in each of said plurality of light cavities, and wherein said plurality of lights is disposed in said plurality of light cavities, respectively.

9. An eyestrain reducing device, comprising:
    a lighting unit having a lighting unit housing;
    wherein said lighting unit housing comprises a first panel; a second panel disposed in generally parallel, spaced-apart relationship with respect to said first panel; a rear panel extending between said first panel and said second panel; a generally planar light panel extending between said first panel and said second panel in spaced-apart relationship with respect to said rear panel; and first, second and third light openings provided in said light panel in spaced-apart relationship with respect to each other;
    first, second and third lights provided in said lighting unit housing adjacent to said first, second and third light openings, respectively;
    wherein said first and third lights are adapted to emit light in the visible light range of the light spectrum and said second light is an infrared light;
    a reflector panel having a plurality of light cavities provided in said lighting unit housing adjacent to said first, second and third light openings, respectively, and a stepped reflector surface provided in each of said plurality of light cavities;
    wherein said first, second and third lights is disposed in said plurality of light cavities, respectively;
    a power source connected to said first, second and third lights;
    a switch provided on said first panel of said lighting unit housing and electrically connected between said power source and said first, second and third lights; and
    an attachment device provided on said second panel.

10. The eyestrain reducing device of claim 9 further comprising a power cord connected to said first, second and third lights and said switch and extending from said lighting unit housing and a plug provided on said power cord.

11. The eyestrain reducing device of claim 9 further comprising a battery compartment provided in said lighting unit housing and wherein said power source comprises a battery provided in said battery compartment.

* * * * *